(12) United States Patent
Guiles et al.

(10) Patent No.: US 6,638,237 B1
(45) Date of Patent: Oct. 28, 2003

(54) LEFT VENTRICULAR CONDUITS AND METHODS FOR DELIVERY

(75) Inventors: Marvin Guiles, Stow, MA (US); Gerald Melsky, Lexington, MA (US)

(73) Assignee: Percardia, Inc., Nashua, NH (US)

( * ) Notice: Subject to any disclaimer, the term of this patent is extended or adjusted under 35 U.S.C. 154(b) by 154 days.

(21) Appl. No.: 09/630,385

(22) Filed: Aug. 1, 2000

Related U.S. Application Data
(60) Provisional application No. 60/147,211, filed on Aug. 4, 1999.

(51) Int. Cl.$^7$ ............................................... A61B 19/00
(52) U.S. Cl. ............................................................. 604/8
(58) Field of Search .......................................... 604/8, 9

(56) References Cited

U.S. PATENT DOCUMENTS

| | | |
|---|---|---|
| 3,971,363 A | 7/1976 | Fletcher et al. |
| 4,503,568 A | 3/1985 | Madras |
| 4,733,665 A | 3/1988 | Palmaz |
| 4,769,029 A | 9/1988 | Patel |
| 4,995,857 A | 2/1991 | Arnold |
| 5,035,702 A | 7/1991 | Taheri |
| 5,135,467 A | 8/1992 | Citron |
| 5,190,058 A | 3/1993 | Jones et al. |
| 5,226,889 A | 7/1993 | Sheiban |
| 5,258,008 A | 11/1993 | Wilk |
| 5,287,861 A | 2/1994 | Wilk |
| 5,292,309 A | 3/1994 | Van Tassel et al. |
| 5,330,486 A | 7/1994 | Wilk |
| 5,344,426 A | 9/1994 | Lau et al. |
| 5,385,541 A | 1/1995 | Kirsch et al. |
| 5,409,019 A | 4/1995 | Wilk |
| 5,423,744 A | 6/1995 | Gencheff et al. |
| 5,423,851 A | 6/1995 | Samuels |
| 5,429,144 A | 7/1995 | Wilk |
| 5,443,497 A | 8/1995 | Venbrux |
| 5,456,694 A | 10/1995 | Marin et al. |
| 5,456,712 A | 10/1995 | Maginot |
| 5,456,714 A | 10/1995 | Owen |
| 5,470,320 A | 11/1995 | Tiefenbrun et al. |

(List continued on next page.)

FOREIGN PATENT DOCUMENTS

| | | |
|---|---|---|
| EP | 0 732 088 | 9/1996 |
| EP | 0 797 957 | 10/1997 |
| EP | 0 824 903 | 2/1998 |

(List continued on next page.)

OTHER PUBLICATIONS

US 6,331,185, 12/2001, Gambale et al. (withdrawn)
Tweden et al., "Ventriculocoronary Artery Bypass (VCAB), a Novel Approach to Myocardial Revascularization" Feb. 2000.

(List continued on next page.)

*Primary Examiner*—J. Casimer Jacyna
(74) *Attorney, Agent, or Firm*—Finnegan, Henderson, Farabow, Garrett & Dunner, LLP

(57) ABSTRACT

Conduits are provided to direct blood flow from the left ventricle to a coronary artery at a location distal to a blockage in the coronary artery. Threaded and nonthreaded conduits are delivered using a guidewire delivered through the posterior and anterior walls of a coronary artery and into the heart wall. A dilator may be provided over the guidewire into the heart wall, and the conduit delivered over the dilator. An introducer sleeve may be provided over the dilator into the heart wall, the dilator removed, and the conduit delivered through the introducer sleeve. A hollow needle also may be inserted into the posterior and anterior walls of the coronary artery prior to inserting the guidewire. A depth measuring tool may determine the appropriate length of the conduit prior to delivery. The depth measuring tool can include the hollow needle with an access port on a proximal end of the needle and an opening on the distal end of the needle in flow communication with the access port so that when the needle is inserted through the heart wall and into the heart chamber, blood flow through the opening.

54 Claims, 21 Drawing Sheets

U.S. PATENT DOCUMENTS

| | | |
|---|---|---|
| 5,527,337 A | 6/1996 | Stack et al. |
| 5,578,075 A | 11/1996 | Dayton |
| 5,593,434 A | 1/1997 | Williams |
| 5,609,626 A | 3/1997 | Quijano et al. |
| 5,611,778 A | 3/1997 | Brinon |
| 5,618,299 A | 4/1997 | Khosravi et al. |
| 5,643,278 A | 7/1997 | Wijay |
| 5,655,548 A | 8/1997 | Nelson et al. |
| 5,662,124 A | 9/1997 | Wilk |
| 5,676,670 A | 10/1997 | Kim |
| 5,733,267 A | 3/1998 | Del Toro |
| 5,755,682 A | 5/1998 | Knudson et al. |
| 5,758,663 A | 6/1998 | Wilk et al. |
| 5,787,933 A | 8/1998 | Russ et al. |
| 5,797,920 A | 8/1998 | Kim |
| 5,810,836 A | 9/1998 | Hussein et al. |
| 5,810,871 A | 9/1998 | Tuckey et al. |
| 5,824,038 A | 10/1998 | Wall |
| 5,824,071 A | 10/1998 | Nelson et al. |
| 5,830,222 A | 11/1998 | Makower et al. |
| 5,843,163 A | 12/1998 | Wall |
| 5,851,232 A | 12/1998 | Lois |
| 5,855,597 A | 1/1999 | Jayaraman |
| 5,865,723 A | 2/1999 | Love |
| 5,876,419 A | 3/1999 | Carpenter et al. |
| 5,878,751 A | 3/1999 | Hussein et al. |
| 5,893,848 A | 4/1999 | Negus et al. |
| 5,908,028 A | 6/1999 | Wilk |
| 5,908,029 A | 6/1999 | Knudson et al. |
| 5,935,119 A | 8/1999 | Guy et al. |
| 5,935,161 A | 8/1999 | Robinson et al. |
| 5,935,162 A | 8/1999 | Dang |
| 5,944,019 A | 8/1999 | Knudson et al. |
| 5,961,548 A | 10/1999 | Shmulewitz |
| 5,968,093 A | 10/1999 | Kranz |
| 5,971,993 A | 10/1999 | Hussein et al. |
| 5,976,153 A | 11/1999 | Fischell et al. |
| 5,976,155 A | 11/1999 | Foreman et al. |
| 5,976,159 A | 11/1999 | Bolduc et al. |
| 5,976,169 A | 11/1999 | Imran |
| 5,976,178 A | 11/1999 | Goldsteen et al. |
| 5,976,181 A | 11/1999 | Whelan et al. |
| 5,976,182 A | 11/1999 | Cox |
| 5,976,192 A | 11/1999 | McIntyre et al. |
| 5,976,650 A | 11/1999 | Campbell et al. |
| 5,979,455 A | 11/1999 | Maginot |
| 5,980,530 A | 11/1999 | Willard et al. |
| 5,980,533 A | 11/1999 | Holman |
| 5,980,548 A | 11/1999 | Evans et al. |
| 5,980,551 A | 11/1999 | Summers et al. |
| 5,980,552 A | 11/1999 | Pinchasik et al. |
| 5,980,553 A | 11/1999 | Gray et al. |
| 5,980,566 A | 11/1999 | Alt et al. |
| 5,984,955 A | 11/1999 | Wisselink |
| 5,984,956 A | 11/1999 | Tweden et al. |
| 5,984,963 A | 11/1999 | Ryan et al. |
| 5,984,965 A | 11/1999 | Knapp et al. |
| 5,989,207 A | 11/1999 | Hughes |
| 5,989,263 A | 11/1999 | Shmulewitz |
| 5,989,287 A | 11/1999 | Yang et al. |
| 5,993,481 A | 11/1999 | Marcade et al. |
| 5,993,482 A | 11/1999 | Chuter |
| 5,997,563 A | 12/1999 | Kretzers |
| 5,997,573 A | 12/1999 | Quijano et al. |
| 6,001,123 A | 12/1999 | Lau |
| 6,004,261 A | 12/1999 | Sinofsky et al. |
| 6,004,347 A | 12/1999 | McNamara et al. |
| 6,004,348 A | 12/1999 | Banas et al. |
| 6,007,543 A | 12/1999 | Ellis et al. |
| 6,007,575 A | 12/1999 | Samuels |
| 6,007,576 A | 12/1999 | McClellan |
| 6,010,530 A | 1/2000 | Goicoechea |
| 6,017,365 A | 1/2000 | Von Oepen |
| 6,029,672 A | 2/2000 | Vanney et al. |
| 6,036,697 A | 3/2000 | DiCaprio |
| 6,039,721 A | 3/2000 | Johnson et al. |
| 6,042,581 A | 3/2000 | Ryan et al. |
| 6,045,565 A | 4/2000 | Ellis et al. |
| 6,053,911 A | 4/2000 | Ryan et al. |
| 6,053,924 A | 4/2000 | Hussein |
| 6,053,942 A | 4/2000 | Eno et al. |
| 6,067,988 A | 5/2000 | Mueller |
| 6,068,638 A | 5/2000 | Makower et al. |
| 6,071,292 A | 6/2000 | Makower et al. |
| 6,076,529 A | 6/2000 | Vanney et al. |
| 6,080,163 A | 6/2000 | Hussein et al. |
| 6,093,166 A | 7/2000 | Knudson et al. |
| 6,095,997 A | 8/2000 | French et al. |
| 6,102,941 A | 8/2000 | Tweden et al. |
| 6,106,538 A | 8/2000 | Shiber |
| 6,110,201 A | 8/2000 | Quijano et al. |
| 6,113,630 A | 9/2000 | Vanney et al. |
| 6,113,823 A | 9/2000 | Eno |
| 6,117,165 A | 9/2000 | Becker |
| 6,123,682 A | 9/2000 | Knudson et al. |
| 6,126,649 A | 10/2000 | Van Tassel et al. |
| 6,139,541 A | 10/2000 | Vanney et al. |
| 6,152,141 A | 11/2000 | Stevens et al. |
| 6,159,225 A | 12/2000 | Makower |
| 6,162,245 A | 12/2000 | Jayaraman |
| 6,165,188 A | 12/2000 | Saadat et al. |
| 6,171,251 B1 | 1/2001 | Mueller et al. |
| 6,171,303 B1 | 1/2001 | Ben-Haim et al. |
| 6,182,668 B1 | 2/2001 | Tweden et al. |
| 6,186,972 B1 | 2/2001 | Nelson et al. |
| 6,190,353 B1 | 2/2001 | Makower et al. |
| 6,193,726 B1 | 2/2001 | Vanney |
| 6,196,230 B1 | 3/2001 | Hall et al. |
| 6,197,050 B1 | 3/2001 | Eno et al. |
| 6,200,310 B1 | 3/2001 | Ben-Haim et al. |
| 6,203,556 B1 | 3/2001 | Evans et al. |
| 6,214,041 B1 | 4/2001 | Tweden et al. |
| 6,223,752 B1 | 5/2001 | Vanney et al. |
| 6,231,587 B1 | 5/2001 | Makower |
| 6,237,607 B1 | 5/2001 | Vanney et al. |
| 6,238,406 B1 | 5/2001 | Ellis et al. |
| 6,248,112 B1 | 6/2001 | Gambale et al. |
| 6,250,305 B1 | 6/2001 | Tweden |
| 6,253,768 B1 | 7/2001 | Wilk |
| 6,254,564 B1 | 7/2001 | Wilk et al. |
| 6,258,119 B1 | 7/2001 | Hussein et al. |
| 6,261,304 B1 | 7/2001 | Hall et al. |
| 6,283,951 B1 | 9/2001 | Flaherty et al. |
| 6,283,983 B1 | 9/2001 | Makower et al. |
| 6,287,317 B1 | 9/2001 | Makower et al. |
| 6,290,719 B1 | 9/2001 | Garberoglio |
| 6,290,728 B1 | 9/2001 | Phelps et al. |
| 6,302,875 B1 | 10/2001 | Makower et al. |
| 6,302,892 B1 | 10/2001 | Wilk |
| 6,306,125 B1 | 10/2001 | Parker et al. |
| 6,330,884 B1 | 12/2001 | Kim |
| 6,331,178 B1 | 12/2001 | Loeb et al. |
| 6,350,248 B1 | 2/2002 | Knudson et al. |
| 6,363,939 B1 | 4/2002 | Wilk |
| 6,375,615 B1 | 4/2002 | Flaherty et al. |
| 6,379,319 B1 | 4/2002 | Garibotto et al. |
| 6,387,119 B2 | 5/2002 | Wolf et al. |
| 2001/0004683 A1 | 6/2001 | Gambale et al. |
| 2001/0004690 A1 | 6/2001 | Gambale et al. |
| 2001/0004699 A1 | 6/2001 | Gittings et al. |
| 2001/0008969 A1 | 7/2001 | Evans et al. |

| | | | |
|---|---|---|---|
| 2001/0025643 A1 | 10/2001 | Foley | |
| 2001/0027287 A1 | 10/2001 | Shmulewitz et al. | |
| 2001/0034547 A1 | 10/2001 | Hall et al. | |
| 2001/0037117 A1 | 11/2001 | Gambale et al. | |
| 2001/0039426 A1 | 11/2001 | Makower et al. | |
| 2001/0039445 A1 | 11/2001 | Hall et al. | |
| 2001/0041902 A1 | 11/2001 | Lepulu et al. | |
| 2001/0047165 A1 | 11/2001 | Makower et al. | |
| 2001/0053932 A1 | 12/2001 | Phelps et al. | |
| 2002/0002349 A1 | 1/2002 | Flaherty et al. | |
| 2002/0004662 A1 | 1/2002 | Wilk | |
| 2002/0032478 A1 | 3/2002 | Boeksteggers et al. | |
| 2002/0045928 A1 | 4/2002 | Boekstegers | |
| 2002/0058897 A1 | 5/2002 | Renati | |

FOREIGN PATENT DOCUMENTS

| | | |
|---|---|---|
| EP | 0 876 803 | 11/1998 |
| EP | 0 903 123 | 3/1999 |
| EP | 0 904 745 | 3/1999 |
| EP | 0 955 017 | 11/1999 |
| EP | 0 955 019 | 11/1999 |
| EP | 0 962 194 | 12/1999 |
| EP | 1 020 166 | 7/2000 |
| EP | 1 027 870 | 8/2000 |
| EP | 1 097 676 A1 | 5/2001 |
| EP | 1 166 721 | 1/2002 |
| GB | 2316322 | 10/1998 |
| WO | WO 94/16629 | 8/1994 |
| WO | WO 96/39962 | 12/1996 |
| WO | 97/13463 | 4/1997 |
| WO | 97/13471 | 4/1997 |
| WO | WO 97/18768 | 5/1997 |
| WO | 97/27893 | 8/1997 |
| WO | 97/27897 | 8/1997 |
| WO | 97/27898 | 8/1997 |
| WO | WO 97/31590 | 9/1997 |
| WO | 97/32551 | 9/1997 |
| WO | WO 97/41916 | 11/1997 |
| WO | WO 97/43961 | 11/1997 |
| WO | WO 98/02099 | 1/1998 |
| WO | 98/06356 | 2/1998 |
| WO | 98/08456 | 3/1998 |
| WO | 98/10714 | 3/1998 |
| WO | 98/16161 | 4/1998 |
| WO | WO 98/17185 | 4/1998 |
| WO | WO 98/19607 | 5/1998 |
| WO | WO 98/25549 | 6/1998 |
| WO | WO 98/38916 | 9/1998 |
| WO | WO 98/38925 | 9/1998 |
| WO | WO 98/44869 | 10/1998 |
| WO | 98/46115 | 10/1998 |
| WO | 98/46119 | 10/1998 |
| WO | WO 98/49964 | 11/1998 |
| WO | WO 98/53759 | 12/1998 |
| WO | WO 98/55027 | 12/1998 |
| WO | WO 98/57591 | 12/1998 |
| WO | 99/08624 | 2/1999 |
| WO | 99/17683 | 4/1999 |
| WO | 99/21490 | 5/1999 |
| WO | WO 99/21510 | 5/1999 |
| WO | WO 99/22655 | 5/1999 |
| WO | 99/25273 | 5/1999 |
| WO | WO 99/32051 | 7/1999 |
| WO | WO 99/35977 | 7/1999 |
| WO | 99/36000 | 7/1999 |
| WO | 99/36001 | 7/1999 |
| WO | WO 99/37218 | 7/1999 |
| WO | 99/38459 | 8/1999 |
| WO | 99/40868 | 8/1999 |
| WO | WO 99/47071 | 9/1999 |
| WO | WO 99/47078 | 9/1999 |
| WO | WO 99/48427 | 9/1999 |
| WO | 99/48545 | 9/1999 |
| WO | WO 99/49790 | 10/1999 |
| WO | 99/49793 | 10/1999 |
| WO | 99/49910 | 10/1999 |
| WO | 99/51162 | 10/1999 |
| WO | WO 99/52481 | 10/1999 |
| WO | 99/53863 | 10/1999 |
| WO | WO 99/55406 | 11/1999 |
| WO | 99/60941 | 12/1999 |
| WO | 99/62430 | 12/1999 |
| WO | 00/09195 | 2/2000 |
| WO | WO 00/10623 | 3/2000 |
| WO | 00/12029 | 3/2000 |
| WO | 00/15146 | 3/2000 |
| WO | 00/15147 | 3/2000 |
| WO | 00/15148 | 3/2000 |
| WO | 00/15149 | 3/2000 |
| WO | 00/15275 | 3/2000 |
| WO | WO 00/18302 | 4/2000 |
| WO | WO 00/18325 | 4/2000 |
| WO | WO 00/18326 | 4/2000 |
| WO | WO 00/18331 | 4/2000 |
| WO | 00/21436 | 4/2000 |
| WO | 00/21461 | 4/2000 |
| WO | 00/21463 | 4/2000 |
| WO | 00/24449 | 5/2000 |
| WO | 00/33725 | 6/2000 |
| WO | WO 00/35376 | 6/2000 |
| WO | WO 00/36997 | 6/2000 |
| WO | 00/41632 | 7/2000 |
| WO | 00/41633 | 7/2000 |
| WO | 00/45711 | 8/2000 |
| WO | WO 00/48530 | 8/2000 |
| WO | WO 00/56224 | 9/2000 |
| WO | WO 00/56225 | 9/2000 |
| WO | 00/56387 | 9/2000 |
| WO | 00/66007 | 11/2000 |
| WO | 00/66009 | 11/2000 |
| WO | 00/66035 | 11/2000 |
| WO | 00/71195 | 11/2000 |
| WO | WO 01/08602 | 2/2001 |
| WO | 01/10340 | 2/2001 |
| WO | 01/10341 | 2/2001 |
| WO | 01/10347 | 2/2001 |
| WO | 01/10348 | 2/2001 |
| WO | 01/10349 | 2/2001 |
| WO | WO 01/26562 | 4/2001 |

OTHER PUBLICATIONS

*American Medical Association Publication;* "Myocardial Revascularization Experiments Using the Epicardium," B. G. Lary, M.D., et al.; *Archives of Surgery,* pp. 69–72, vol. 98, No. 1, Jan. 1969.

*The Journal of Thoracic and Cardiovascular Surgery,* "Experimental Evalution of Direct Transventicular Revascularization," L. Kuzela, M.D., et al., pp. 770–773, vol. 57, Jan.–Jun. 1969, The C.V. Mosby Co., St. Louis, MO.

*The Journal of Thoracic and Cardiovascular Surgery,* "Myocardial Revascularization by a New Method of Carrying Blood Directly from the Left Ventricular Cavity into the Coronary Circulation," C Massimo, M.D., et al., pp. 257–264, Aug. 1957.

*The Journal of Thoracic and Cardiovascular Surgery,* "Experimental Evaluation of Myocardial Tunnelization as a Method of Myocardial Revascularization," I. Anabtawi, M.D., et al., pp. 638–646., Nov. 1969.

*The Journal of Thoracic and Cardiovascular Surgery,* "The Possibility of Myocardial Revascularization by Creation of a Left Ventriculocoronary Artery Fistula," I. Munro, M.D., et al., pp. 25–32., vol. 58, 1969.

*AJR,* "Expandable Inrahepatic Portacoval Shunt Stents in Dogs with Chronic Portal Hypertension," J. Palmaz, et al., pp. 1251–1256, Dec., 1988.

*AJR,* "Expandable Intrahepatic Portacaval Shunt Stents: Early Experience in the Dog," J. Palmaz, et al., pp. 821–825.

*American Heart Journal,* "Effects of Laser Irradiation Delivered by Flexible Fiberoptic System on the Left Ventricular Internal Myocardium," G. Lee, M.D., et al., pp. 587–590, vol. 106, No. 3, Sep. 1983.

*Texas Heart Institute Journal,* "Transmyocardial Laser Revascularization," D. Cooley, M.D., et al., pp. 220–224, vol. 21, No. 3, 1994.

*American Journal of Physiology,* "Transmural Myocardial Perfusion During Restricted Coronary Inflow in the Awake Dog," R. Bache, et al., pp. H645–651, vol. 232, No. 6 ISSN–0002–9513.

*The Annals of Thoracic Surgery,* "Myocardial Canalization," A. Khazei, M.D., et al., vol. 6, No. 2, Aug. 1968.

*Surgical Forum,* "Proceedings of the 24th Annual Sessions of the Forum on Fundamental Surgical Problems," 54th Clinical Congress of the American College of Surgeons, Chicago, Illinois, Oct., 1968, pp. 156–159, American College of Surgeons, Chicago, Illinois.

PULL OUT FORCES OF VARIOUS THREADED SCREWS

| DESCRIPTION | THREADS PER INCH | HEIGHT OF THREADS | SHAFT DIAMETER | AVERAGE PULL OUT FORCE (LBS) |
|---|---|---|---|---|
| DRYWALL SCREW | 15 | 0.023 | 0.093 | 1.80 |
| DRYWALL SCREW | 15 | 0.024 | 0.088 | 1.80 |
| DRYWALL SCREW | 8 | 0.028 | 0.122 | 1.75 |
| HEX BOLT | 30 | 0.015 | 0.132 | <0.250 |
| SHEET METAL SCREW | 10 | 0.032 | 0.156 | 3.00 |

FIG. 14

PULL OUT FORCES OF BARBED SHUNTS

| DESCRIPTION (ALL BARBS ARE ANNULAR) | NUMBER OF BARBS | BARB SPACING | BARB WIDTH (IN) | BARB DIAMETER | BARB HEIGHT (IN) | AVERAGE REMOVAL FORCE (LBS) |
|---|---|---|---|---|---|---|
| ANGLED BARBS FACING ONE DIRECTION | 3 | 0.140 | 0.040 | 0.110 | 0.0065 | 0.38 |
| CONTINUOUS ANGLED BARBS, NO SPACING BETWEEN EACH ONE | 8 | NONE | 0.068 | 0.109 | 0.0055 | 0.42 |
| ANGLED BARBS FACING ONE DIRECTION, FLANGE AT ONE END (TESTED IN DIFFERENT HEART) | 6 | NONE | 0.085 | 0.108 | 0.0065 | 0.13 |
| FLAT BARBS | 4 | 0.062 | 0.049 | 0.108 | 0.0060 | 0.29 |
| FLAT BARBS | 2 | 0.140 | 0.054 | 0.110 | 0.0065 | 0.25 |
| STENT ANGLED AT ONE END, FLAT BARBS, FLANGE AT OPPOSITE END (TESTED IN DIFFERENT HEART) | 3 | 0.094 | 0.097 | 0.109 | 0.0035 | <.13 |
| CONTROL SAMPLE | NONE | NONE | NONE | NONE | NONE | ~0 |

*ALL INSERTION FORCES ARE APPROXIMATELY 1.0 LB
*THE APPROXIMATE WALL THICKNESS OF THE LEFT VENTRICLE IS .67-.84 IN, NEAR THE APEX OF THE HEART IT IS APPROXIMATELY .51 IN

*FIG. 15*

PULL THROUGH FORCES FOR FLANGES THROUGH ARTERIAL WALL

| DESCRIPTION | WIDTH (IN) | LENGTH (IN) | AVERAGE PULL THROUGH FORCE (LBS) |
|---|---|---|---|
| SHALLOW FLANGE, BARBED STENT, NO SPACES BETWEEN EACH BARB | 0.114 | 0.169 | 0.50 |
| SHALLOW FLANGE, FLAT BARBED STENT, OPPOSITE END ANGLED | 0.097 | 0.132 | 0.50 |
| DEEP FLANGE, FLAT STENT | 0.108 | 0.159 | 1.00 |
| VERY LONG AND DEEP FLANGE, FLAT STENT | 0.109 | 0.195 | 1.50 |
| FLAT STENT WITH ANGLED END, FLANGE TUBE SHAPED WITH OPENING IN THE MIDDLE | 0.094 | 0.182 | 0.75 |
| CIRCULAR FLANGE, FLAT STENT | | 0.169 R | 0.75 |

*FIG. 16*

LEFT VENTRICULAR CONDUITS AND METHODS FOR DELIVERY

REFERENCE TO RELATED APPLICATIONS

This application claims the benefits of U.S. Provisional Application No. 60/147,211, filed Aug. 4, 1999.

FIELD OF THE INVENTION

The present invention relates to an apparatus for bypassing a blocked or stenosed blood vessel segment, and, more particularly, to an apparatus and method for delivering a conduit between the coronary artery and the left ventricle of the heart.

BACKGROUND OF THE INVENTION

Coronary artery disease is a major problem in the U.S. and throughout the world. Coronary arteries as well as other blood vessels frequently become clogged with plaque which, at the very least, can reduce blood and oxygen flow to the heart muscle (myocardium), and may impair the efficiency of the heart's pumping action, and can lead to heart attack (myocardial infarction) and death. In some cases, these coronary arteries can be unblocked through non-invasive techniques such as balloon angioplasty. In more difficult cases, a surgical bypass of the blocked vessel is necessary.

In a coronary bypass operation, one or more venous segments are inserted between the aorta and the coronary artery, or, alternatively, the distal end of an internal mammary artery is anastomosed to the coronary artery at a site distal to the stenosis or occlusion. The inserted venous segments or transplants act as a bypass of the blocked portion of the coronary artery and thus provide for a free or unobstructed flow of blood to the heart. More than 500,000 bypass procedures are performed in the U.S. every year.

Such coronary artery bypass graft (CABG) surgery, however, is a very intrusive procedure which is expensive, time-consuming, and traumatic to the patient. The operation requires an incision through the patient's sternum (sternotomy), and that the patient be placed on a heart-lung bypass pump so that the heart can be operated on while not beating. A saphenous vein graft is harvested from the patient's leg, another highly invasive procedure, and a delicate surgical procedure is required to piece the bypass graft to the coronary artery (anastpmosis). Hospital stays subsequent to the surgery and convalescence are prolonged. Furthermore, many patients are poor surgical candidates due to other concomitant illnesses.

As mentioned above, another conventional treatment is percutaneous transluminal coronary angioplasty (PTCA) or other types of angioplasty. However, such vascular treatments are not always indicated due to the type or location of the blockage or stenosis, or due to the risk of emboli.

Thus, there is a need for an improved coronary bypass system which is less traumatic to the patient.

SUMMARY OF THE INVENTION

Briefly stated, the methods and apparatus described and illustrated herein generally relate to direct coronary revascularization, wherein a conduit or opening is provided from the left ventricle to the coronary artery, often times the left anterior descending (LAD), to provide blood flow directly therethrough. These methods and apparatus are particularly useful when a blockage partially or completely obstructs the coronary artery, in which case the bypass conduit or opening is positioned distal to the blockage. More preferably, conduits are provided to direct blood flow from the left ventricle to a coronary artery at a location distal to a blockage in the coronary artery. The conduits may be threaded to facilitate insertion into a patient's heart wall and to control the depth of insertion. Threaded and nonthreaded conduits are preferably delivered using a guidewire approach. In this approach, the guidewire is placed through a needle that is inserted into the left ventricle. After the guidewire is placed, the needle is removed. In one embodiment, a dilator is provided over the guidewire into the heart wall, and the conduit is delivered over the dilator. In another embodiment, an introducer sleeve is provided over the dilator into the heart wall, the dilator is removed, and the conduit is delivered through the introducer sleeve. A depth measuring tool is preferably used to determine the appropriate length of the conduit prior to delivery. In another embodiment, a feature can be included on the end of the introducer sleeve that engages with the arterial wall, and when pulled back, distends the artery. The conduit can then be advanced until the deployable flanges seat against the bottom of the artery.

BRIEF DESCRIPTION OF THE DRAWINGS

FIG. 14 is a table of the pull out forces of various threaded conduits that may be used according to certain embodiments of the present invention.

FIG. 15 is a table of pull out forces of various barbed conduits that may be used according to certain embodiments of the present invention.

FIG. 16 is a table of push-through forces of various conduits having flanges that may be used according to certain embodiments of the present invention.

DETAILED DESCRIPTION OF THE PREFERRED EMBODIMENT

Figure 1:
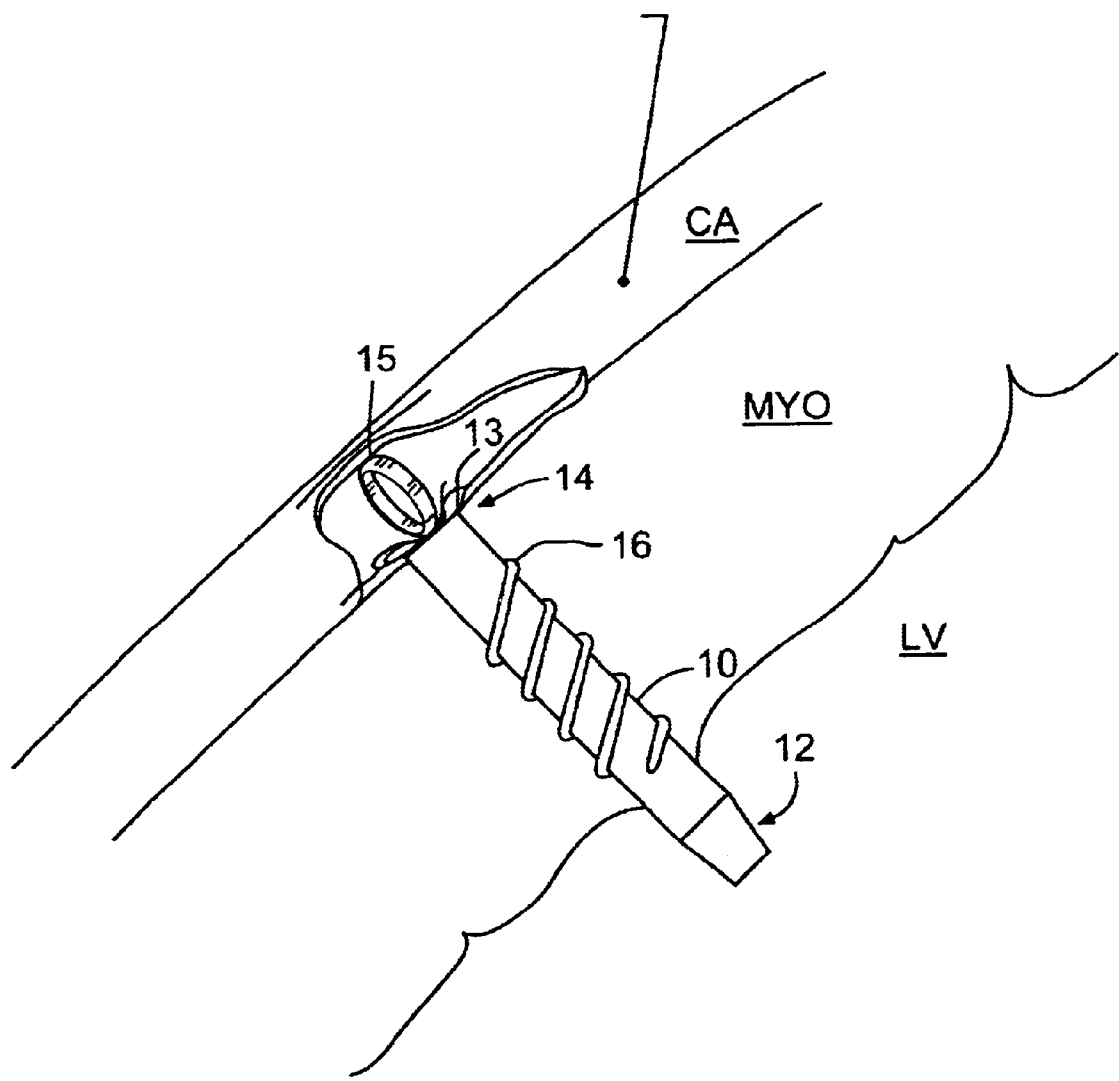
FIG. 1 is a schematic side view of a threaded conduit inserted into a heart wall of a patient between the left ventricle and a coronary artery according to a preferred embodiment of the present invention.

As is well known, the coronary artery branches off the aorta and is positioned along the external surface of the heart wall. Oxygenated blood that has returned from the lungs to the heart then flows from the heart to the aorta. Some blood in the aorta flows into the coronary arteries, and the remainder of blood in the aorta flows on to the rest of the body. The coronary arteries are the primary blood supply to the heart muscle and are thus critical to life. In some individuals, atherosclerotic plaque, aggregated platelets, and/or thrombi build up within the coronary artery, blocking the free flow of blood and causing complications ranging from mild angina to heart attack and death. The presence of coronary vasospasm, also known as "variant angina" or "Prinzmetal's angina," compounds this problem in many patients.

The principles of the present invention are not limited to left ventricular conduits, and include conduits for communicating bodily fluids from any space within a patient to another space within a patient, including any mammal. Furthermore, such fluid communication through the conduits is not limited to any particular direction of flow and can be antegrade or retrograde with respect to the normal flow of fluid. Moreover, the conduits may communicate between a bodily space and a vessel or from one vessel to another vessel (such as an artery to a vein or vice versa). Moreover, the conduits can reside in a single bodily space so as to communicate fluids from one portion of the space to another. For example, the conduits can be used to achieve a bypass within a single vessel, such as communicating blood from a proximal portion of an occluded coronary artery to a more distal portion of that same coronary artery.

In addition, the conduits and related methods can preferably traverse various intermediate destinations and are not limited to any particular flow sequence. For example, in one preferred embodiment of the present invention, the conduit communicates from the left ventricle, through the myocardium, into the pericardial space, and then into the coronary artery. However, other preferred embodiments are disclosed, including direct transmyocardial communication from a left ventricle, through the myocardium and into the coronary artery. Thus, as emphasized above, the term "transmyocardial" should not be narrowly construed in connection with the preferred fluid communication conduits, and other non-myocardial and even non-cardiac fluid communication are preferred as well. With respect to the walls of the heart (and more specifically the term "heart wall"), the preferred conduits and related methods are capable of fluid communication through all such walls including, without limitation, the pericardium, epicardium, myocardium, endocardium, septum, etc.

The bypass which is achieved with certain preferred embodiments and related methods is not limited to a complete bypass of bodily fluid flow, but can also include a partial bypass which advantageously supplements the normal bodily blood flow. Moreover, the occlusions which are bypassed may be of a partial or complete nature, and therefore the terminology "bypass" or "occlusion" should not be construed to be limited to a complete bypass or a complete occlusion but can include partial bypass and partial occlusion as described.

The preferred conduits and related methods disclosed herein can also provide complete passages or partial passages through bodily tissues. In this regard, the conduits can comprise stents, shunts, or the like, and therefore provide a passageway or opening for bodily fluid such as blood. Moreover, the conduits are not necessarily stented or lined with a device but can comprise mere tunnels or openings formed in the tissues of the patient.

The conduits of the present invention preferably comprise both integral or one-piece conduits as well as plural sections joined together to form a continuous conduit. The present conduits can be deployed in a variety of methods consistent with sound medical practice including vascular or surgical deliveries, including minimally invasive techniques. For example, various preferred embodiments of delivery rods and associated methods may be used. In one embodiment, the delivery rod is solid and trocar-like. It may be rigid or semi-rigid and capable of penetrating the tissues of the patient and thereby form the conduit, in whole or in part, for purposes of fluid communication. In other preferred embodiments, the delivery rods may be hollow so as to form the conduits themselves (e.g., the conduits are preferably self-implanting or self-inserting) or have a conduit mounted thereon (e.g., the delivery rod is preferably withdrawn leaving the conduit installed). Thus, the preferred conduit device and method for installation is preferably determined by appropriate patient indications in accordance with sound medical practices.

FIG. 1 illustrates schematically a threaded conduit according to one preferred embodiment of the present invention. The conduit 10 is preferably an elongate tubular body having a proximal end 12 and a distal end 14 and a lumen (not shown) extending therethrough. The proximal end 12 preferably tapers to the desired internal diameter (ID) of the device. The majority of the conduit 10 is threaded with threads 16 to facilitate insertion of the conduit into the heart, as described below. In one preferred embodiment, the entire body of the conduit 10 is threaded except for the proximal tip 12 of the conduit. The conduit may or may not have flange-like features 13 on its distal end that engage with the artery lumen. In addition, the conduit may or may not have a ring 15 for engaging the artery and allowing blood to pass therethrough. FIG. 1 illustrates the conduit 10 as implanted in a patient, wherein the conduit preferably extends between the left ventricle LV, through the myocardium MYO and into the coronary artery CA.

Figure 2:
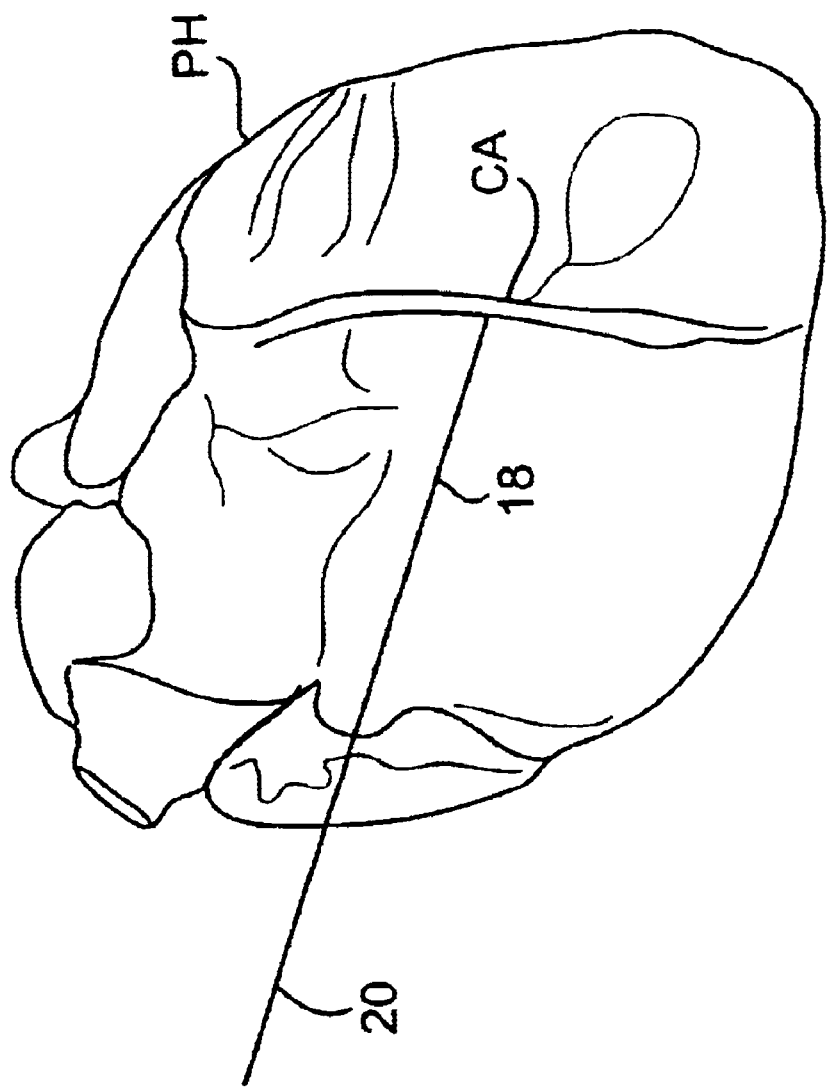
FIG. 2 is a side view of a heart having a needle inserted through a coronary artery to the left ventricle, and a guidewire inserted therethrough.
Figure 2A:
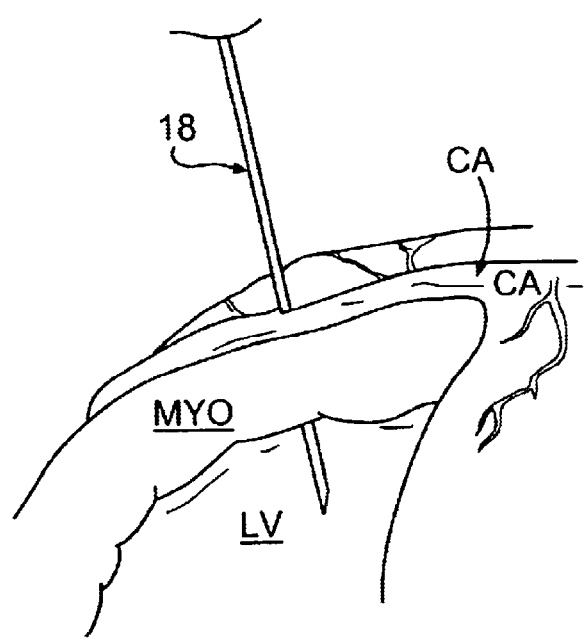
FIG. 2A is a side view showing a needle being inserted through a coronary artery into the left ventricle.

FIGS. 2–5 illustrate one embodiment for delivering the conduit 10 into a patient. Although these figures illustrate a pig heart, it will be appreciated that the methods described herein apply to human hearts as well. To deliver the conduit 10 into the myocardium of the heart PH, a needle 18, as shown in FIG. 2, is first inserted through the heart wall into the left ventricle (also illustrated in FIG. 2A). The needle 18 is preferably hollow, and is preferably inserted through an anterior wall and then a posterior wall of the coronary artery CA. After the needle is inserted, access to the left ventricle may be verified. If it is necessary to relocate the needle, the needle leaves only a very small hole upon removal.

Figure 2B:
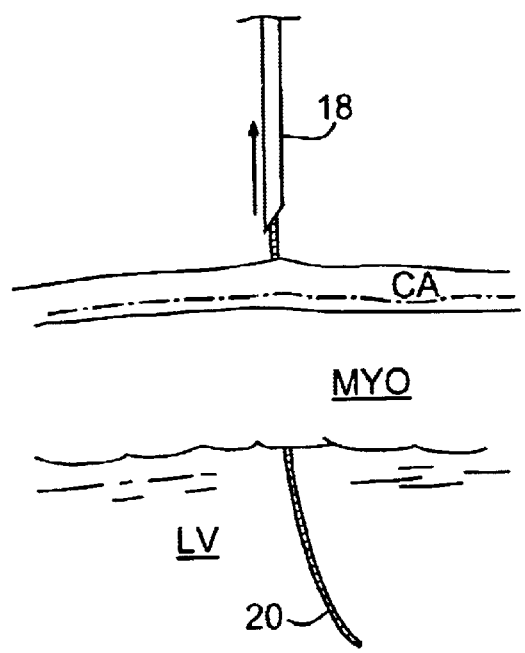
FIG. 2B is a side view of a guidewire inserted through the needle of FIG. 2A, with the needle being removed.

As shown in FIG. 2, after the needle is placed in the left ventricle, a guidewire 20 is inserted into the lumen in the needle. The guidewire is preferably a 0.014 guidewire, which extends into the left ventricle through the needle. After placement of the guidewire the needle is removed, as illustrated in FIG. 2B.

Figure 3:
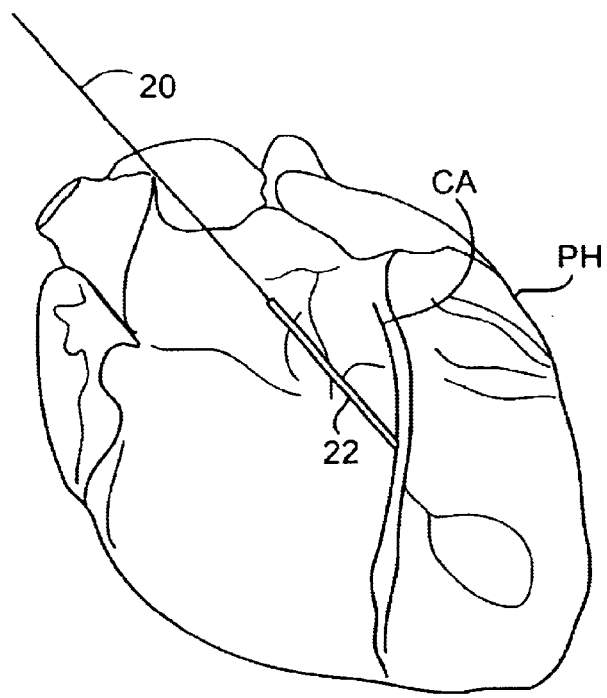
FIG. 3 is a side view of a dilator being inserted over the guidewire of FIG. 2.
Figure 3A:
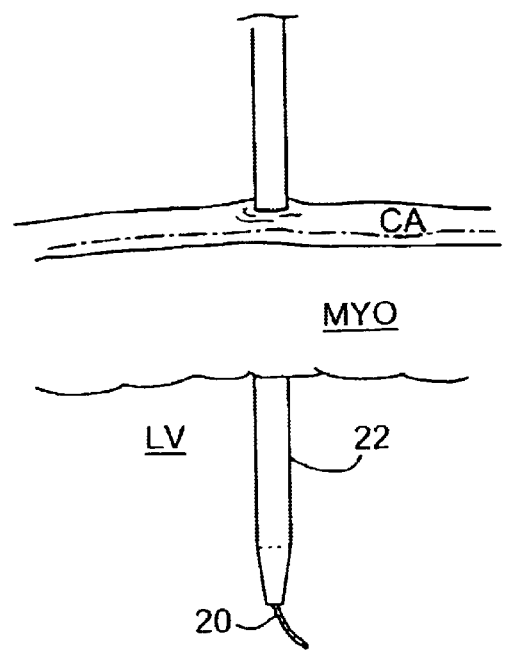
FIG. 3A is a side view of an introducer being advanced over the guidewire of FIG. 2B.

As shown in FIGS. 3 and 3A, a dilator or introducer 22 is preferably inserted over the guidewire and into the heart until the dilator reaches the left ventricle. Upon reaching this position, the guidewire 20 is removed from the heart.

Figure 4:
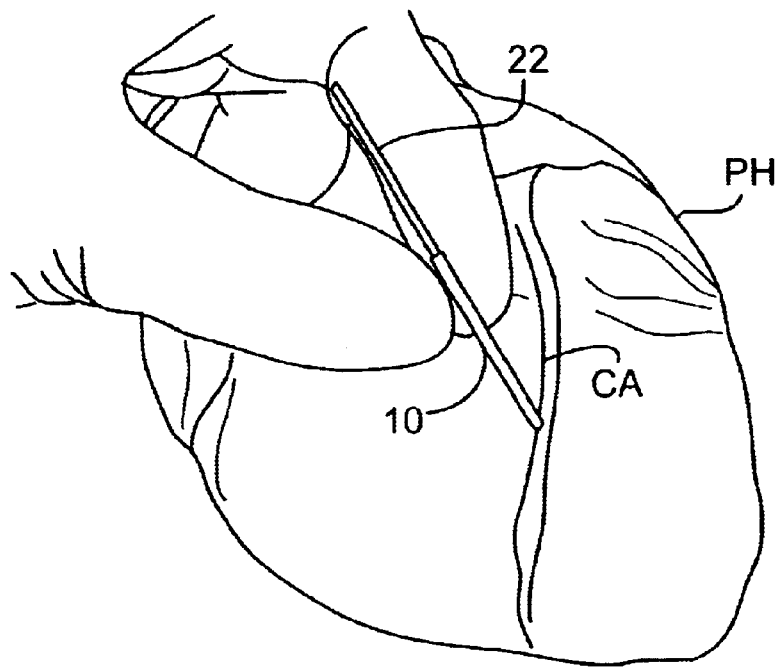
FIG. 4 is a side view of a threaded conduit being inserted over the dilator of FIG. 3.
Figure 4A:
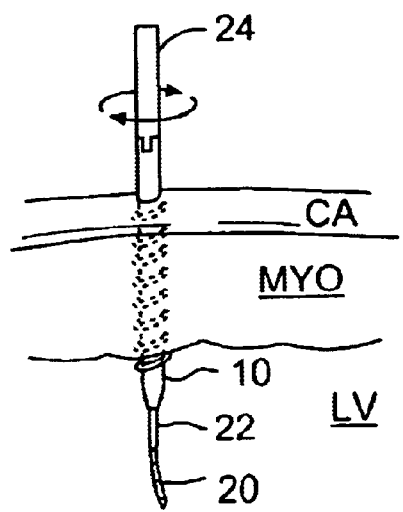
FIG. 4A is a side view of a tool being used to insert a threaded conduit inserted over the dilator of FIG. 3A.

As shown in FIGS. 4 and 4A, a threaded conduit 10, such as described with respect to FIG. 1 above, is placed over the dilator. The non-threaded tapered tip 12 (shown in FIG. 1) of the conduit is inserted into the coronary artery. The conduit 10 is then preferably pulled back to open the artery. The first few threads are then advanced by twisting the threaded conduit. The conduit 10 may be in the form of a shunt.

Figure 5:
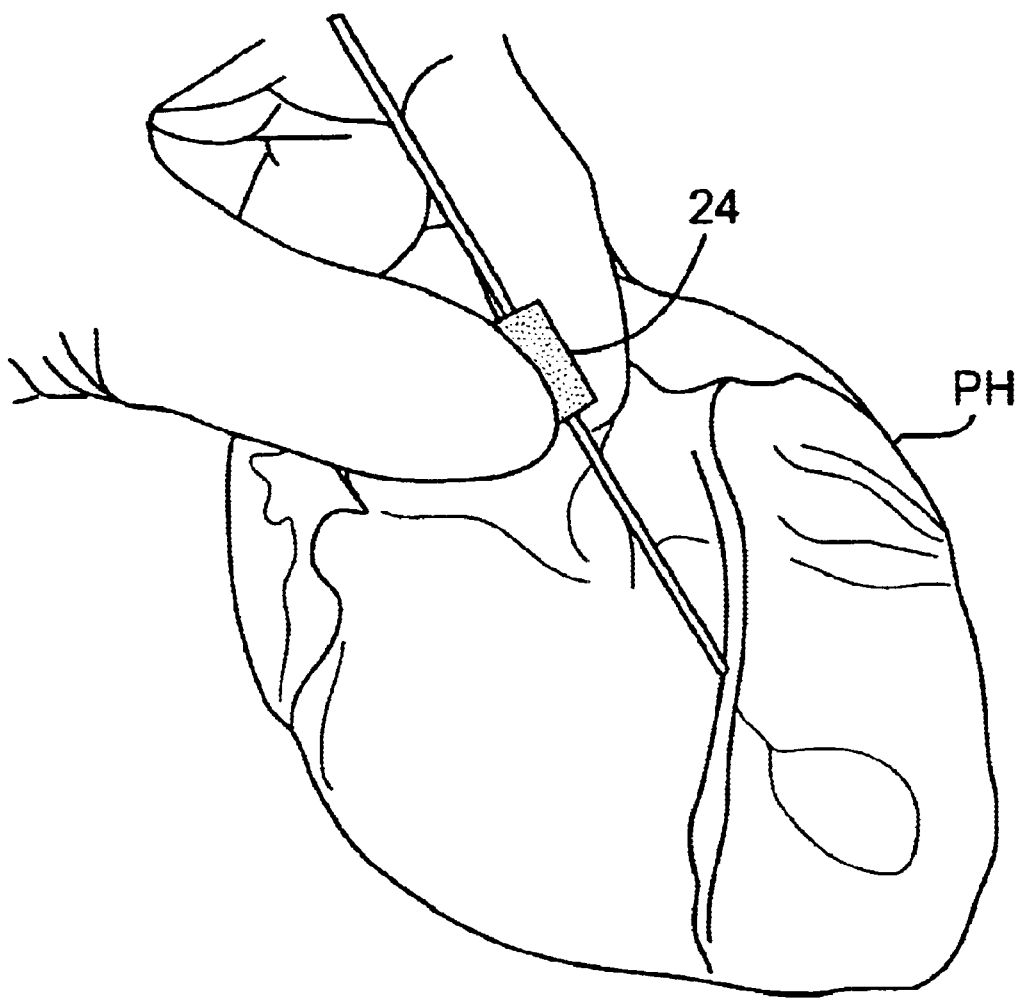
FIG. 5 is a side view showing the threaded conduit of FIG. 4 being advanced into position.

A tool 24 is then used to advance the conduit 10 to the proper depth, as shown in FIGS. 5 and 4A. More preferably, the tool 24 mates with the distal end of the conduit in order to turn the conduit. Because the conduit 10 is threaded, the tool 24 can easily adjust the conduit to a desired depth. After the conduit 10 reaches the desired depth, the tool and the dilator are removed, leaving the conduit 10 in place.

Figure 5A:
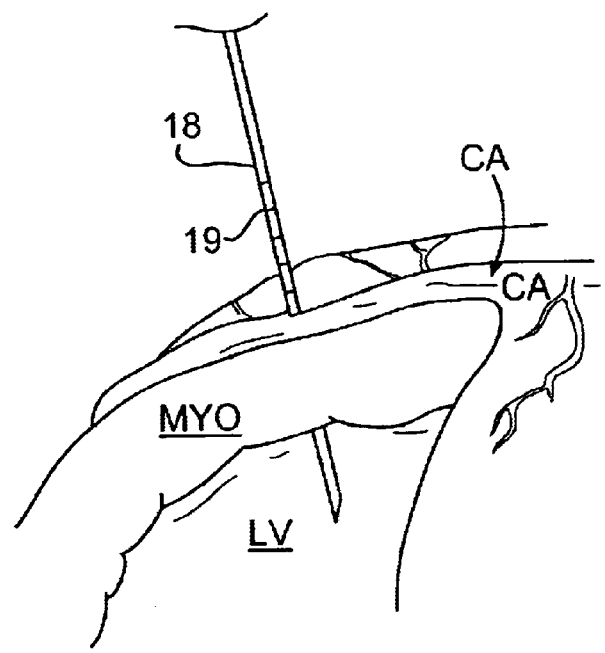
FIGS. 5A–5D are the side views of FIGS. 2A, 2B, 3A and 4A, more particularly showing features included on the needle, introducer and deployment tool that aid in determining the proper deployment depth.
Figure 5B:
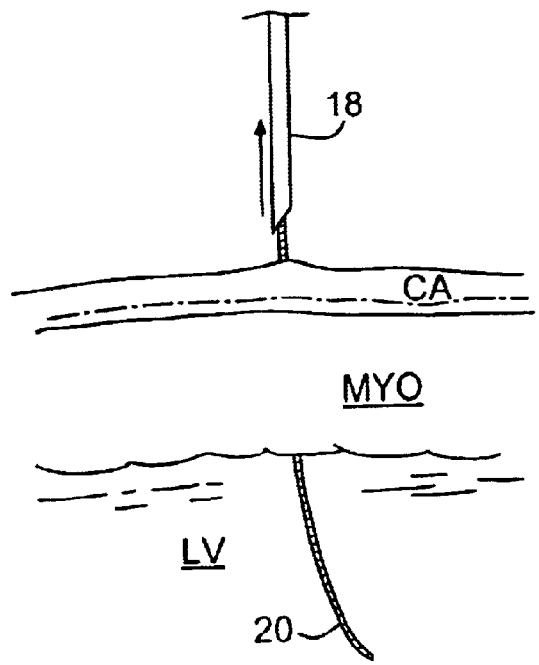
Figure 5C:
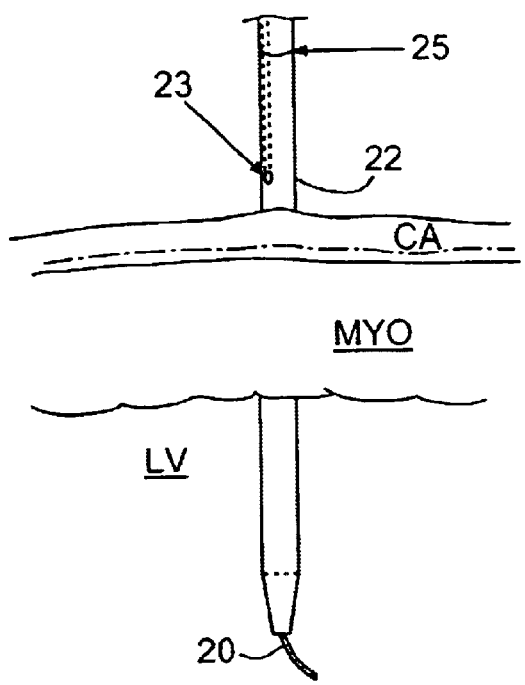
Figure 5D:
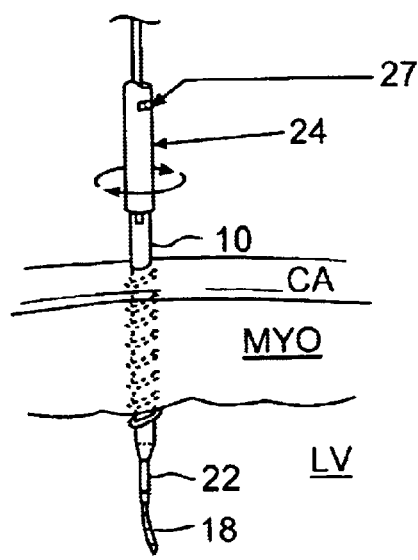

In FIGS. 5A–5D, features are shown on the components of the delivery system illustrated in FIGS. 2A, 2B, 3A and 4A to help determine the proper depth to insert the device. As shown in FIG. 5A, depth markers 19 on the needle 18 can be used to determine the thickness of the myocardium, and ensure that the device used will reach the left ventricle. As shown in FIGS. 5C and 5D, a bleed hole 23 in the dilator/introducer 22 can be used to determine the location of the lumen of the artery, and a depth marker 25 on the dilator/introducer, coupled with a window 27 in the deployment tool 24, can be used to determine when the threaded device 10 has been inserted to the proper depth.

Figure 6:
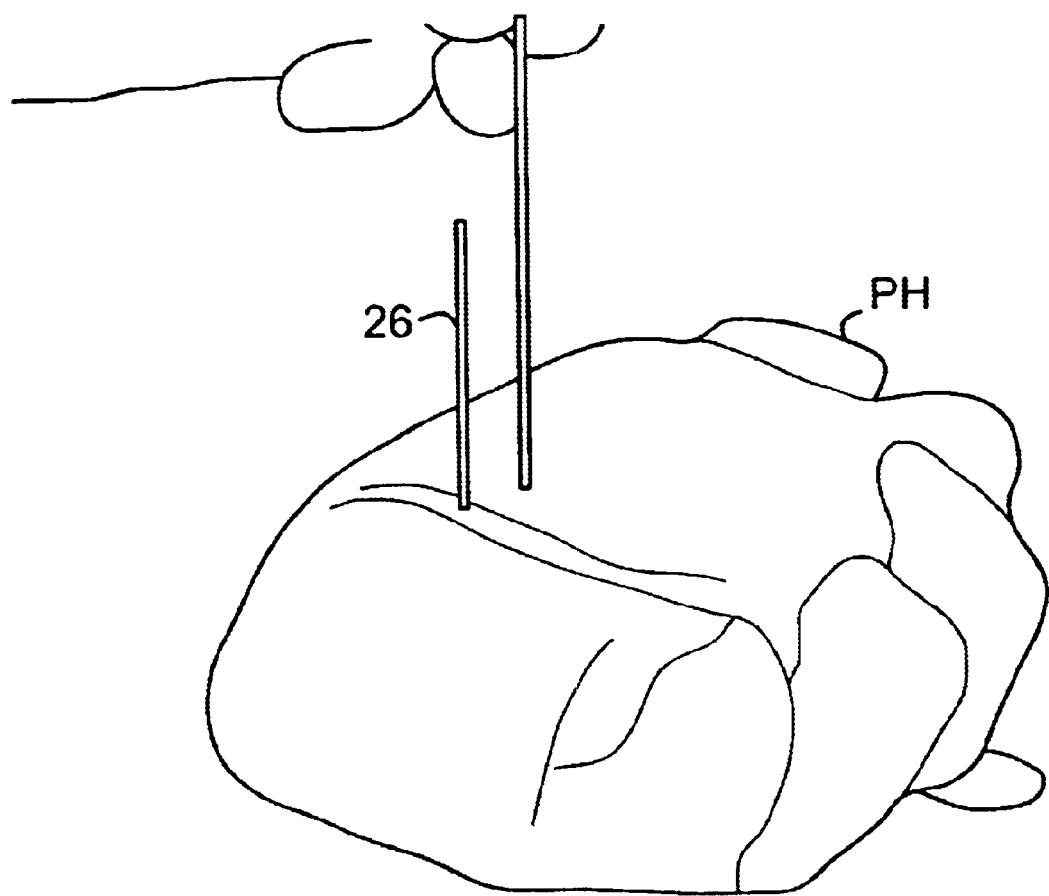
FIG. 6 is a side view of a sleeve being placed for shunt insertion.
Figure 7A:
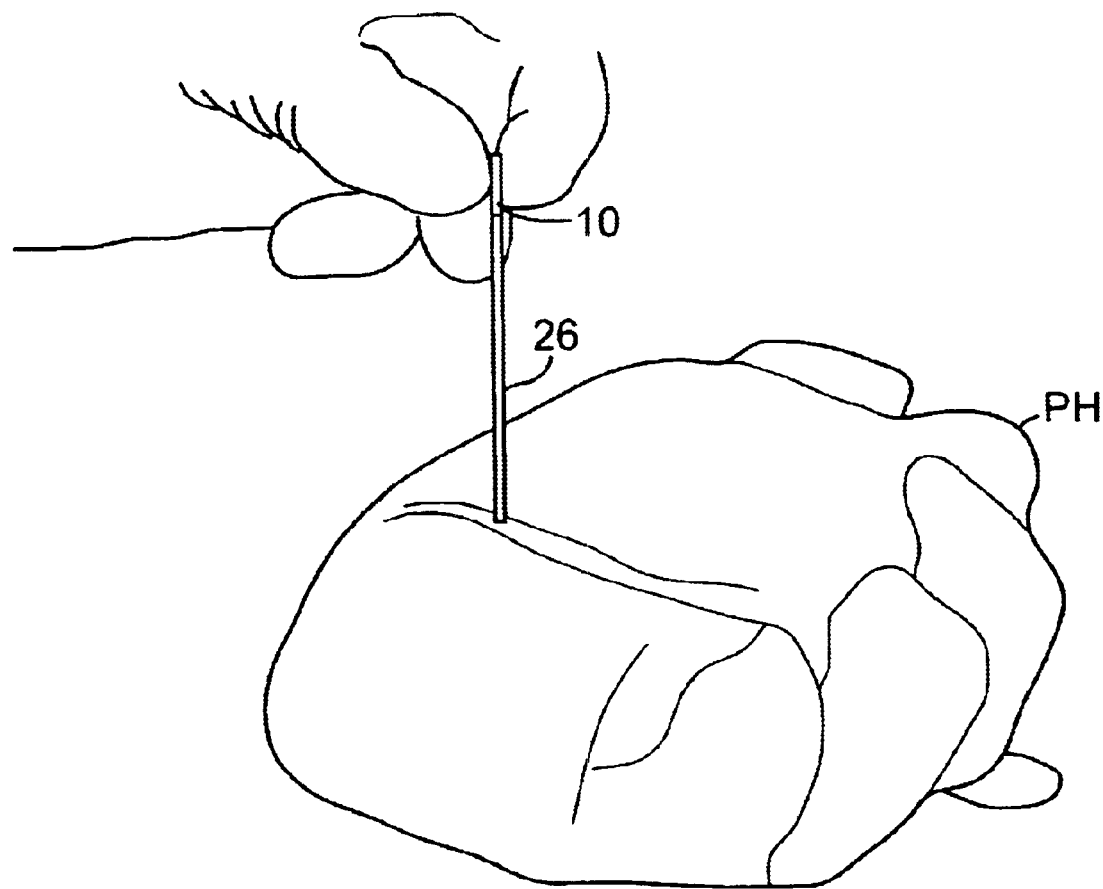
FIG. 7A is a side view of a conduit being inserted through the sleeve of FIG. 6 using a stylet.
Figure 7B:
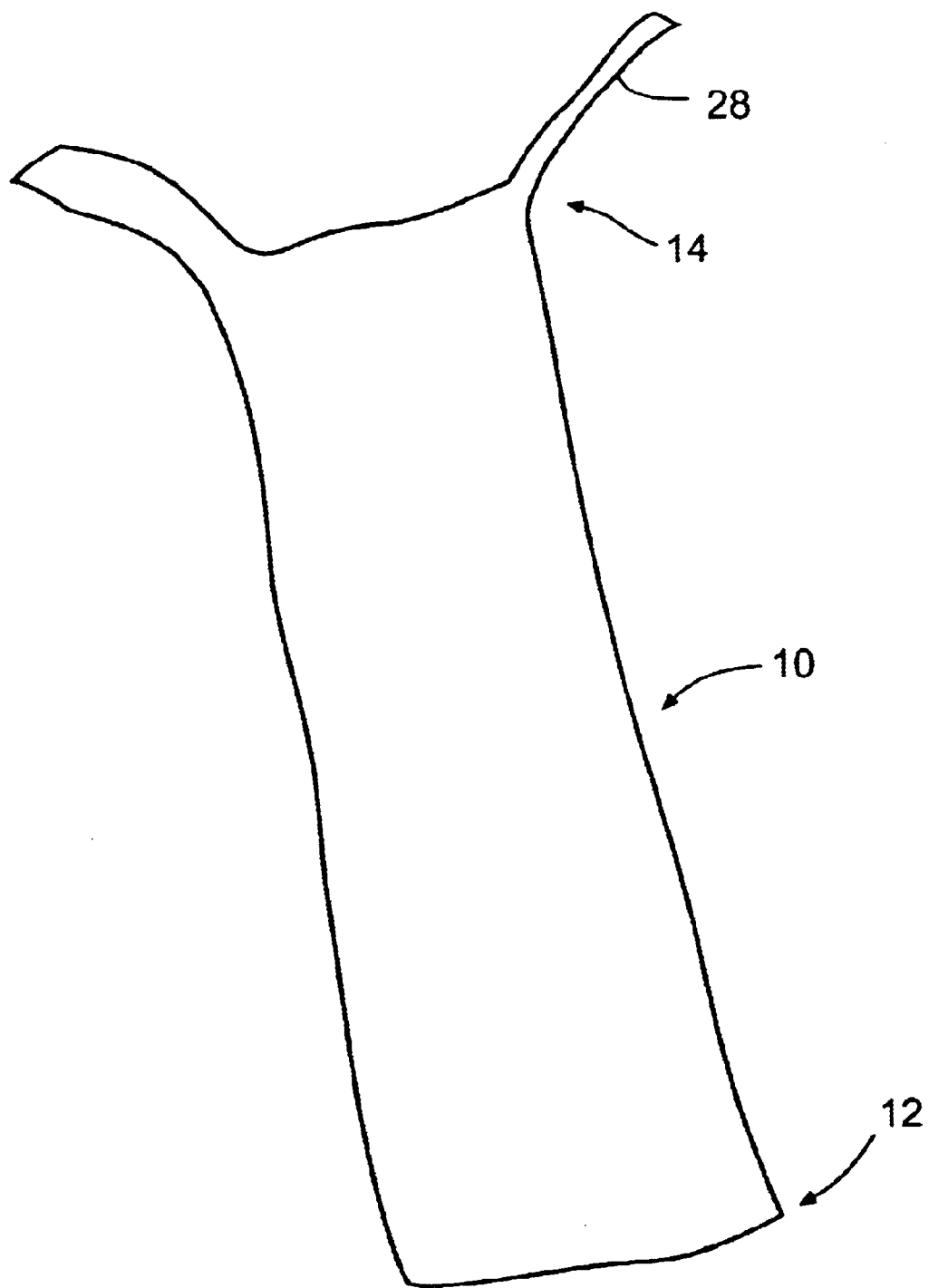
FIG. 7B illustrates the conduit of FIG. 7A having flanges.
Figure 8:
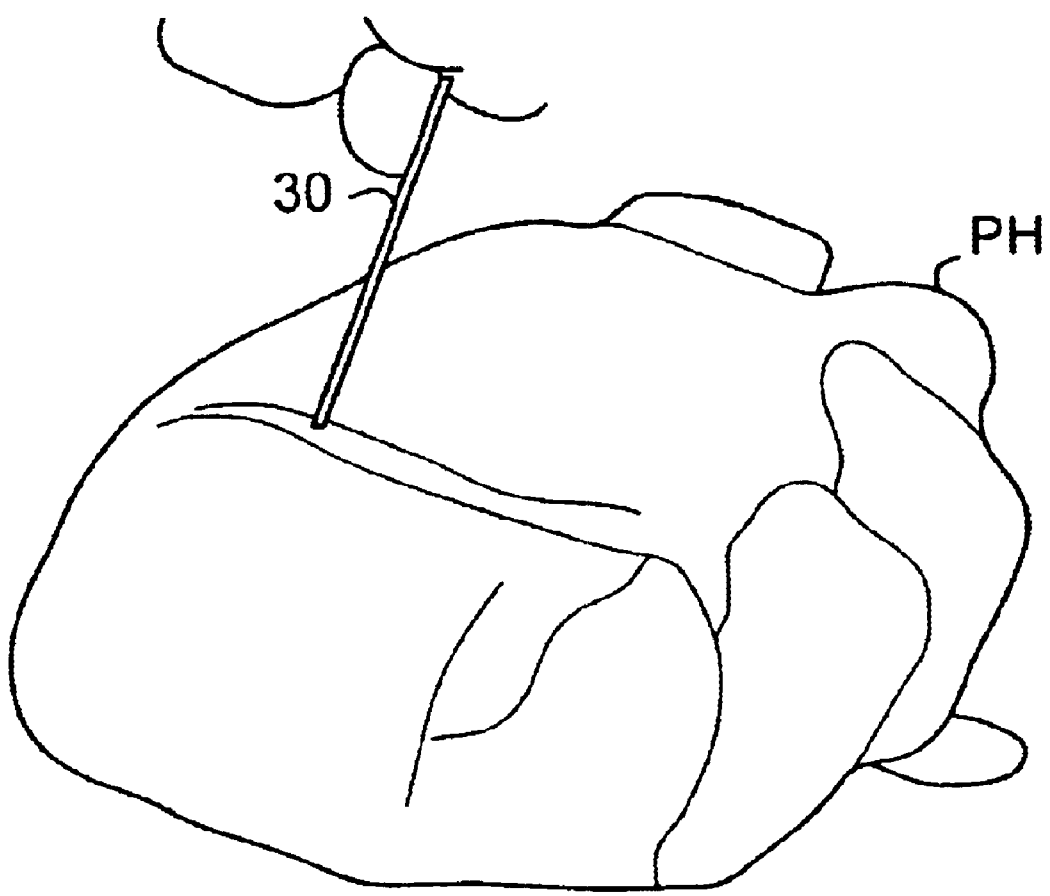
FIG. 8 is a side view of the stylet and sleeve of FIG. 7A being removed.

FIGS. 6–8 illustrate another embodiment for delivering a conduit into a patient's heart, where the conduit need not be threaded. As described and shown with respect to FIGS. 2 and 3 above, a dilator is preferably placed into the heart through the coronary artery using a needle and a guidewire. As shown in FIG. 6, a sleeve 26 is placed over the dilator and inserted into the patient's heart. The dilator is then removed.

As shown in FIG. 7A, a conduit 10 is inserted into the sleeve 26. The conduit may be in the form of a shunt, as illustrated in FIG. 7A. The conduit, as shown in FIG. 7B, may have flanges 28 on its distal end 14 which will assist in anchoring the conduit 10 to the artery. The conduit 10 is placed in the sleeve 26 by collapsing the flanges 28 into the sleeve. The conduit is advanced using a stepped stylet 30, as shown in FIG. 8, to the proper depth. This depth may be determined using an external depth measuring gauge. Holding the stylet 30 stationary, the sleeve is removed, releasing the flanges 28, preferably in the artery CA. Then the stylet is removed, leaving the conduit 10 in place.

Figure 8A:
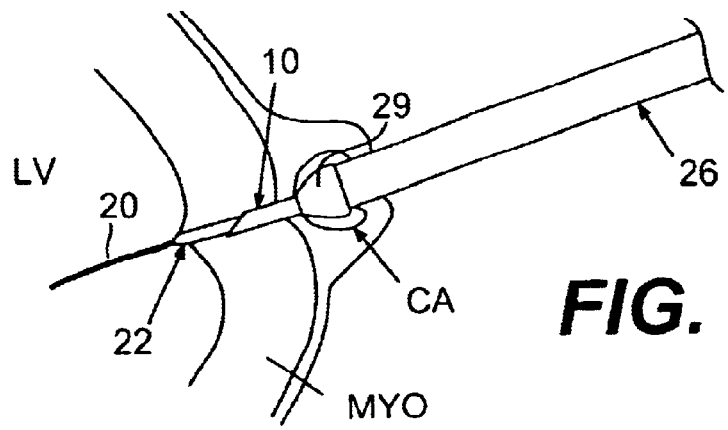
FIGS. 8A–8C are side views of a delivery system for a nonthreaded conduit illustrating a bulb feature on the outer introducer sleeve that aids in holding the artery open and achieving proper placement of the device.
Figure 8B:
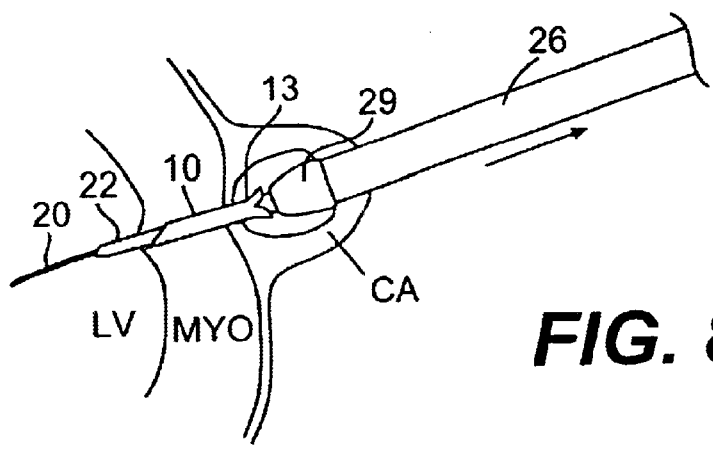
Figure 8C:
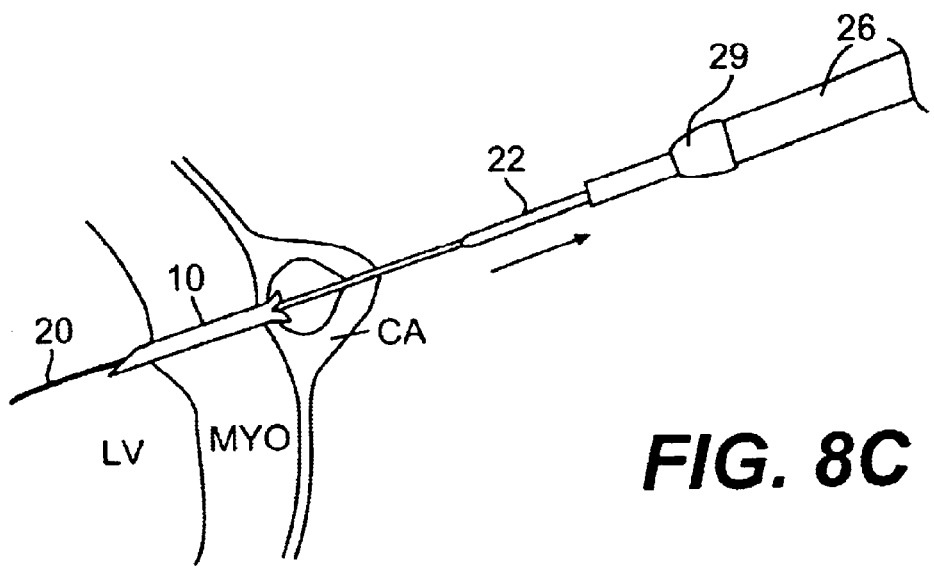

In FIGS. 8A–8C, another embodiment for inserting a non-threaded conduit is shown, wherein a bulbous feature is included on a sleeve for holding the artery open.

In this embodiment, the dilator 22, conduit 10, and sleeve 26 are assembled as shown, and inserted through the coronary artery and into the myocardium until the bulbous feature 29 is inside the lumen of the artery. The assembly is then pulled back, so that the bulbous feature 29 distends the artery. The stepped dilator 22 is then pushed into the left ventricle, advancing the conduit 10 while the sleeve 26 is held in place. The flanges 28 then deploy outside the sleeve, but inside the artery. The conduit can be advanced until the flanges bottom out on the bottom wall of the artery, then the sleeve 26 and dilator 22 can be removed. Several configurations of bulbous features can be incorporated, including a short threaded section, a balloon, or any deployable features that extend past the outer diameter (OD) of the sleeve thereby anchoring the sleeve in the lumen of the artery. It is also understood that the dilator, conduit, and sleeve can be inserted as an assembly, or individually in which case the conduit is backloaded into the sleeve after the sleeve has been placed.

It will be appreciated that various conduit configurations can be used in accordance with the embodiments of the present invention. For instance, threaded conduits, conduits with barbs and conduits with flanges may all be used. FIG. 14 shows a table of the pull out forces of various threaded conduits that may be used. FIG. 15 shows a table of the pull out forces of various barbed conduits that may be used. FIG. 16 shows a table of the push-through forces of various conduits having flanges that may be used.

Figure 9:
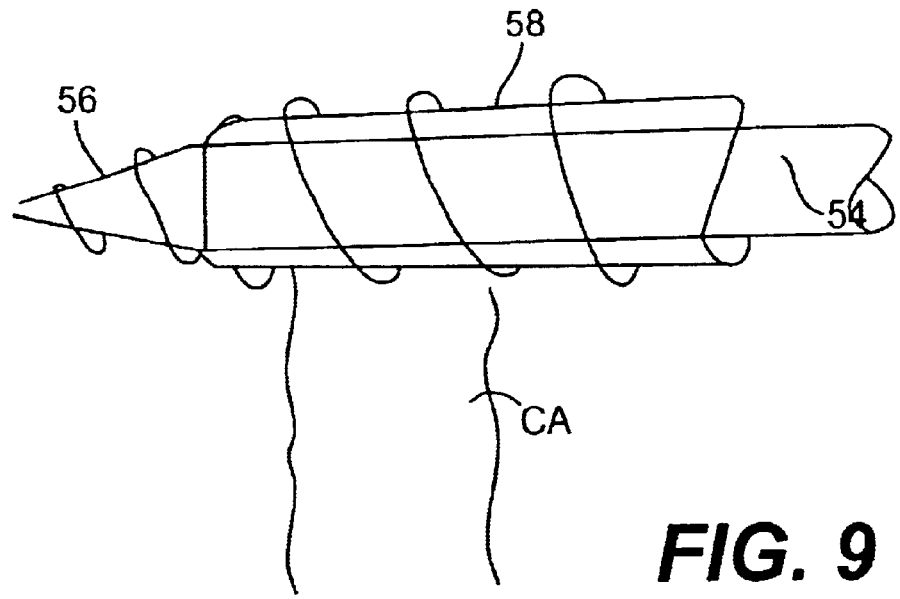
FIG. 9 is a schematic side view of a two piece threaded stylet and sleeve.

FIG. 9 illustrates a two piece threaded stylet and sleeve for delivery of a conduit. The stylet 54 is preferably threaded only on its distal tip 56 which is to be inserted into the myocardium MYO to the left ventricle. The sleeve 58 is preferably threaded over its entire body. The stylet 54 and the sleeve 58 are preferably threaded simultaneously into the myocardium. The stylet is then removed, and a conduit (not shown) for providing blood flow between the left ventricle and coronary artery is inserted through the sleeve while the threads on the sleeve hold the artery open. After insertion of the conduit the sleeve is removed. Alternatively, the threaded sleeve can function as the conduit itself.

In another embodiment, not shown, a method is provided for insertion of a curved conduit. This embodiment is useful where it is desired to provide a curved conduit between the left ventricle and coronary artery. A curved stylet is preferably inserted into the heart wall from the coronary artery to the left ventricle. A nonthreaded conduit is advanced over the curved stylet using a threaded flexible tool placed over the conduit. The threaded flexible tool is preferably attached to the conduit in order to advance the conduit over the stylet. The conduit is inserted by turning the tool until the conduit is in its desired location. In this embodiment, the conduit can be rigid or flexible.

Figure 10:
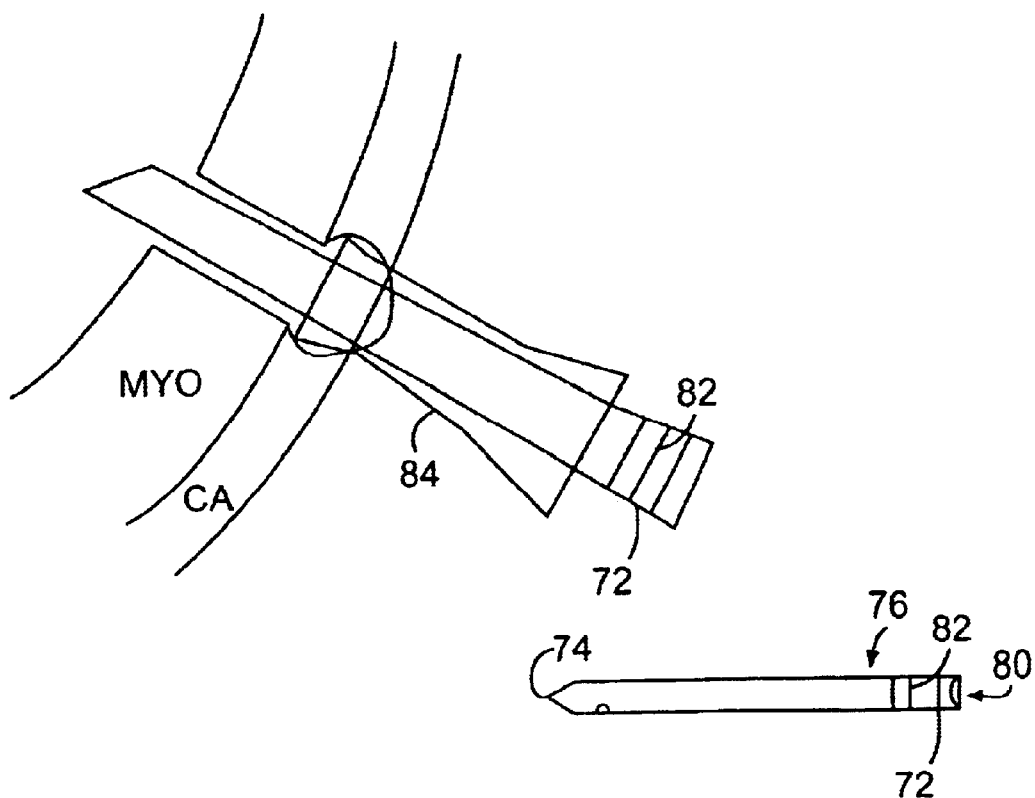
FIG. 10 is a schematic side view of a depth measuring tool.

FIG. 10 illustrates a depth measuring tool 72 for measuring the depth of the coronary artery and/or myocardium. In one embodiment, the tool 72 has a proximal end 74 with an access port 78 in fluid communication with an opening 80 on the distal end 76. Also on the distal end are markers 82 used to measure the depth of insertion of the access port 78. The proximal end is preferably tapered, and is inserted into the myocardium to the left ventricle. When the access port reaches the left ventricle, blood flows through the port and out the opening. At this point the depth of the myocardium can be determined with the markers 82. A bypass conduit 84 can then be inserted over the tool, the conduit having a length determined based on the depth d of the myocardium measured by the tool 72.

Figure 11:
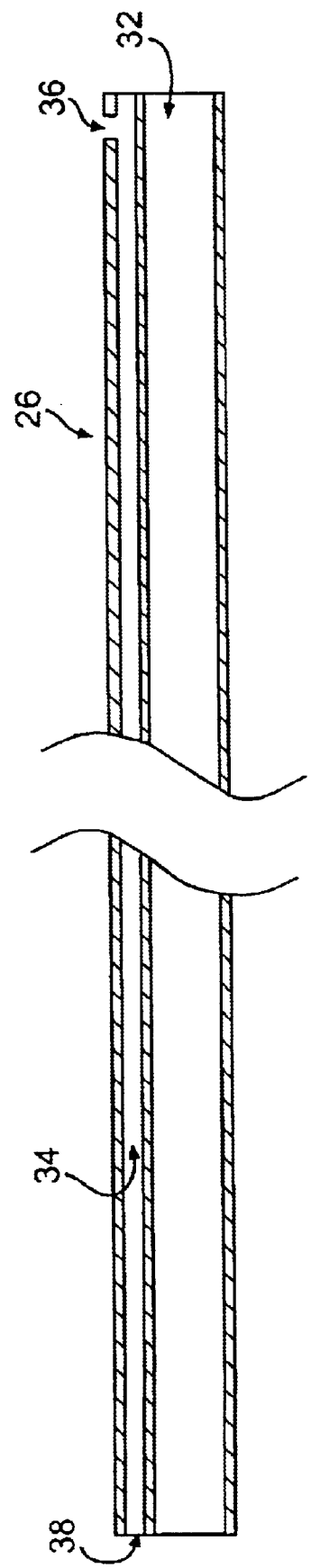
FIG. 11 is a cross-sectional view of an introducer sleeve having a side lumen for depth measurement.

In another embodiment shown in FIG. 11, a depth measuring tool may be implemented within an introducer sleeve 26 such as described above. In this embodiment, the sleeve 26 has a main lumen 32 for introduction of the conduit as described above, and also has a secondary lumen 34 in fluid communication with an access port 36 for measuring the depth of insertion of the introducer sleeve. For instance, when the sleeve 26 is inserted through the heart wall toward the left ventricle, when the sleeve reaches the left ventricle blood flows through the access port and out an opening 38 on the opposite end. Once this location is reached, markers provided on the outside of the sleeve, as described with respect to FIG. 10, are used to determine the desired size of the conduit to be inserted through the lumen 32. It will be appreciated that the depth measuring tools described above may be calibrated so that the access port is located in the coronary artery to indicate positioning therein.

Figure 12A:
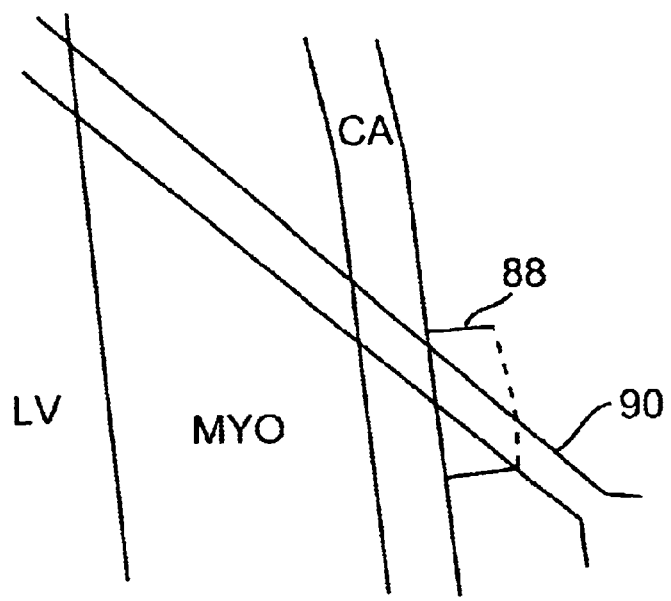
FIGS. 12A–12D are schematic side views of the delivery of a conduit from the coronary artery to the left ventricle using a dilator and introducer.
Figure 12B:
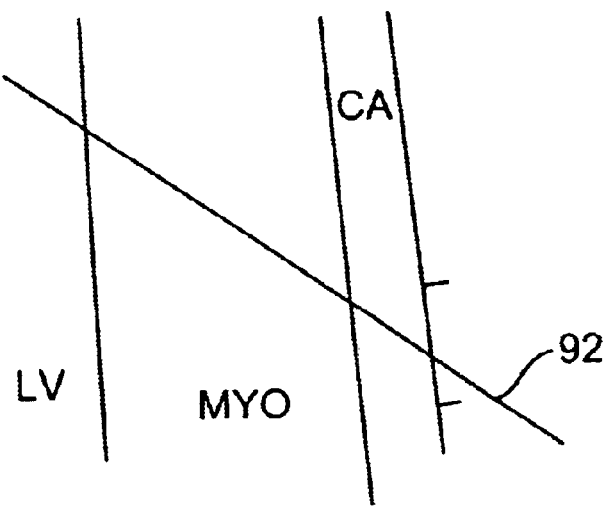
Figure 12C:
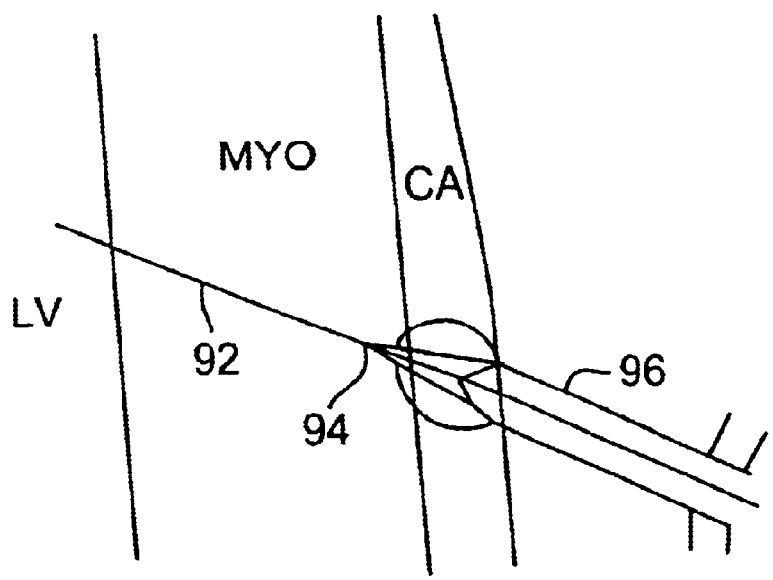
Figure 12D:
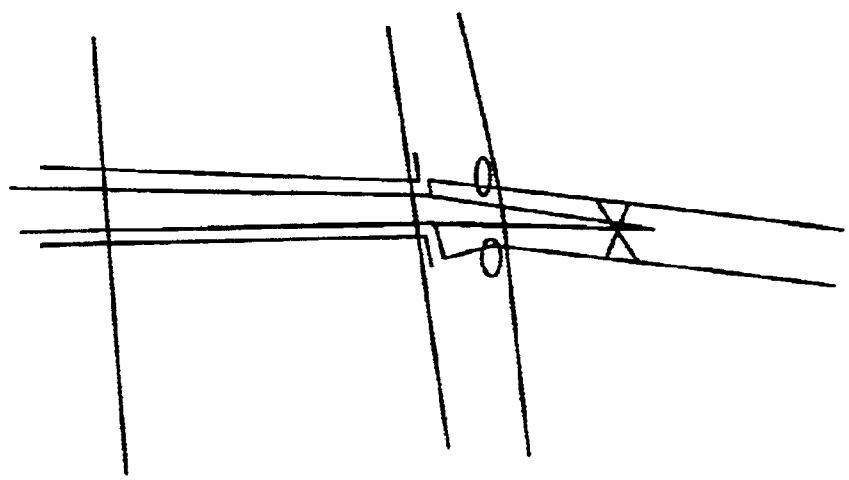

FIGS. 12A–12D illustrate the delivery of a conduit 86 using a dilator and an introducer according to another embodiment of the present invention. As shown in FIG. 12A, a template 88 is placed on the outside of the heart for positioning and a needle 90 is inserted therethrough into the coronary artery, through the myocardium and into the left ventricle. The needle 90 is hollow, and a guidewire 92 is inserted through the needle to the left ventricle, as shown in FIG. 12B. A dilator 94 is loaded onto the guidewire into the myocardium, as shown in FIG. 12C. An introducer sheath 96 is advanced over the dilator until the end of the sheath is in the artery lumen. The artery is opened, and the dilator 94 is removed. As shown in FIG. 12D, the conduit 86 is advanced through the introducer sheath, with a pusher or stylet 98 to advance the conduit into the myocardium.

Figure 13A:
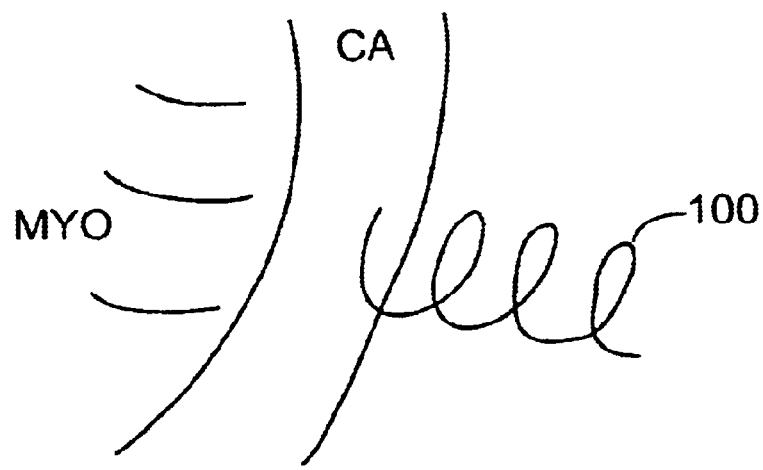
FIGS. 13A–13B are schematic side views of threads used to hold open the coronary artery.
Figure 13B:
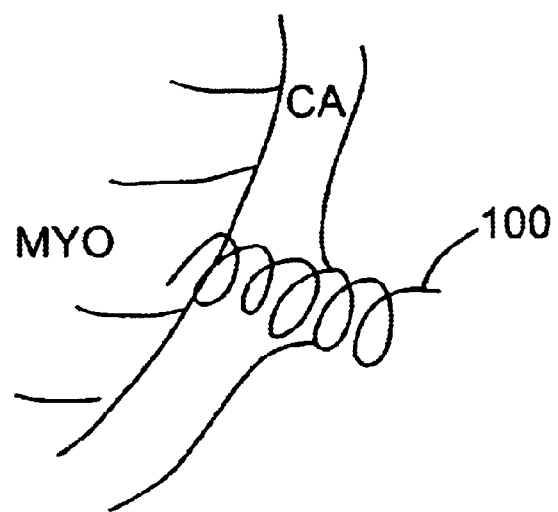

In another embodiment, shown in FIGS. 13A and 13B, coarse threads are used on a device or a tool to hold open the artery. As shown in FIG. 13A, threads 100 which are exemplarily shown are used to penetrate the outer wall of the coronary artery. These threads may be independent as shown, or may be part of a conduit or delivery tool or other member. After the threads penetrate the wall, the threads or the device on which they are attached are pulled back to open the artery. Threading continues as shown in FIG. 13B through the inner wall of the coronary artery.

The embodiments illustrated and described above are provided merely as examples of certain preferred embodiments of the present invention. Other changes and, modifications can be made from the embodiments presented herein by those skilled in the art without departure from the spirit and scope of the invention, as defined by the appended claims.

What is claimed is:

1. A method of delivering a conduit into a heart wall between a heart chamber and an adjacent blood vessel, comprising:
   inserting a hollow needle through an anterior wall and a posterior wall of the blood vessel through the heart wall and into the heart chamber;
   inserting a guidewire through the hollow needle into the heart chamber;
   removing the hollow needle;
   inserting a dilator over the guidewire into the heart wall;
   removing the guidewire; and
   placing a conduit over the dilator into the heart wall.

2. The method of claim 1, further comprising measuring a thickness of the heart wall; prior to placing the conduit.

3. The method of claim 1, further comprising determining if the needle has entered the heart chamber.

4. The method of claim 3, wherein the determining includes providing an access port near a proximal end of the needle and an opening in flow communication with the access port near a distal end of the needle such that blood enters the access port and exits the opening when the access port on the needle has been inserted into the heart chamber.

5. A method of delivering a conduit into a heart wall between a heart chamber and an adjacent blood vessel, comprising:
   inserting a hollow needle through an anterior wall and a posterior wall of the blood vessel through the heart wall and into the heart chamber;
   inserting a guidewire through the hollow needle into the heart chamber;
   removing the hollow needle;
   inserting a dilator over the guidewire into the heart wall;
   removing the guidewire; and
   placing a conduit over the dilator into the heart wall,
   wherein placing the conduit includes screwing the conduit into the heart wall.

6. The method of claim 5, further comprising measuring a thickness of the heart wall prior to placing the conduit.

7. The method of claim 5, further comprising determining if the needle has entered the heart chamber.

8. The method of claim 7, wherein the determining includes providing an access port near a proximal end of the needle and an opening in flow communication with the access port near a distal end of the needle such that blood enters the access port and exits the opening when the access port on the needle has been inserted into the heart chamber.

9. A method of providing direct blood flow between a heart chamber and a coronary vessel, the method comprising:
   placing a guide device through an anterior wall and a posterior wall of the coronary vessel and through a heart wall between the heart chamber and the coronary vessel;
   forming a passageway in the heart wall at a location defined by the guide device;
   placing a conduit within the passageway; and
   delivering via the guide device a first mechanism for forming the passageway and a second mechanism for placing the conduit within the passageway.

10. The method of claim 9, wherein the first and second mechanisms are delivered via the guide device to the heart simultaneously.

11. The method of claim 9, wherein the first mechanism is delivered via the guide device to the heart and, after the first mechanism is removed from the heart via the guide device, the second mechanism is delivered via the guide device to the heart.

12. The method of claim 9, further comprising measuring a distance from the anterior wall of the coronary vessel to the heart chamber prior to placing the guide device.

13. The method of claim 9, wherein the guide device is a guidewire.

14. A method for inserting a conduit into a heart wall between a heart chamber and the coronary artery, comprising:
   screwing a stylet having a threaded tip and a nonthreaded body portion into the heart wall;
   screwing an outer sleeve having a threaded exterior over the nonthreaded body portion of the stylet;
   removing the stylet; and
   inserting the conduit into the heart wall through the outer sleeve.

15. A method for advancing a device into the heart wall of a patient through a coronary artery, comprising:
   screwing a threaded device into the coronary artery to open the artery;
   pulling back on the artery; and
   screwing the threaded device into the heart wall.

16. A method of delivering a conduit into a heart wall between a heart chamber and an adjacent blood vessel, comprising:

inserting a hollow needle into the heart wall through the blood vessel into the heart chamber;

inserting a guidewire through the hollow needle into the heart chamber;

removing the hollow needle;

inserting a dilator over the guidewire into the heart wall;

removing the guidewire; and screwing a threaded conduit over the dilator into the heart wall.

17. A method of providing direct blood flow between a heart chamber and a coronary vessel, the method comprising:

placing a guide device through an anterior wall and a posterior wall of the coronary vessel and through a heart wall between the heart chamber and the coronary vessel;

forming a passageway in the heart wall at a location defined by the guide device by inserting a dilator over the guide device at the location; and placing a conduit within the passageway, wherein the conduit is positioned over the dilator for placement within the passageway.

18. The method of claim 17, further comprising inserting a hollow needle through the anterior wall and posterior wall of the coronary vessel and the heart wall prior to placing the guide device.

19. The method of claim 18, wherein the guide device is a guidewire and placing the guide device includes inserting the guidewire through the hollow needle until an end of the guidewire rests in the heart chamber.

20. The method of claim 19, further comprising removing the hollow needle after inserting the guidewire through the hollow needle.

21. The method of claim 18, further comprising measuring a depth of insertion of the hollow needle.

22. The method of claim 21, wherein measuring the depth of insertion includes viewing a depth indication mechanism on the exterior of the needle.

23. The method of claim 22, wherein the depth indication mechanism includes at least one marking.

24. The method of claim 17, further comprising placing the guide device at an angle relative to the posterior wall of the coronary vessel.

25. The method of claim 24, wherein placing the guide device at the angle includes inserting a hollow needle at the angle through the anterior wall and the posterior wall of the coronary vessel and the heart wall prior to placing the guide device.

26. The method of claim 25, further comprising inserting the hollow needle through a guide template when inserting the hollow needle at the angle.

27. The method of claim 17, wherein the dilator is configured as a sleeve.

28. The method of claim 27, further comprising inserting a sheath over the dilator.

29. The method of claim 28, wherein placing the conduit includes inserting the conduit into the sheath.

30. The method of claim 17, further comprising inserting a sheath in the passageway.

31. The method of claim 30, wherein placing the conduit includes inserting the conduit into the sheath.

32. The method of claim 17, further comprising measuring a distance from the anterior wall of the coronary vessel to the heart chamber prior to placing the guide device.

33. The method of claim 17, wherein the guide device is a guidewire.

34. The method of claim 17, wherein the dilator includes a bleed hole.

35. The method of claim 17, wherein the dilator includes a depth indication mechanism.

36. The method of claim 17, wherein the conduit is threaded.

37. The method of claim 17, wherein the conduit is nonthreaded.

38. The method of claim 17, wherein the conduit is in position over the dilator during the inserting of the dilator.

39. A method of providing direct blood flow between a heart chamber and a coronary vessel, the method comprising:

placing a guide device through an anterior wall and a posterior wall of the coronary vessel and through a heart wall between the heart chamber and the coronary vessel;

forming a passageway in the heart wall at a location defined by the guide device; and placing a conduit within the passageway by screwing the conduit into the heart wall.

40. The method of claim 39, further comprising inserting a hollow needle through the anterior wall and posterior wall of the coronary vessel and the heart wall prior to placing the guide device.

41. The method of claim 39, further comprising placing the guide device at an angle relative to the posterior wall of the coronary vessel.

42. The method of claim 39, wherein forming the passageway includes dilating the heart wall.

43. The method of claim 39, further comprising measuring a distance from the anterior wall of the coronary vessel to the heart chamber prior to placing the guide device.

44. The method of claim 39, wherein the guide device is a guidewire.

45. A method of providing direct blood flow between a heart chamber and a coronary vessel, the method comprising:

positioning a guide device external to the coronary vessel and moving a distal tip of the guide device toward an external surface of an anterior wall of the coronary vessel;

placing the guide device through at least one wall of the coronary vessel and through a heart wall between the heart chamber and the coronary vessel;

forming a passageway in the heart wall at a location defined by the guide device by inserting a dilator over the guide device at the location; and placing a conduit within the passageway, wherein the conduit is positioned over the dilator for placement within the passageway.

46. The method of claim 45, wherein the guide device is placed through the anterior wall of the coronary vessel and a posterior wall of the coronary vessel.

47. The method of claim 45, further comprising inserting a hollow needle through the at least one wall and the heart wall prior to placing the guide device.

48. The method of claim 45, further comprising placing the guide device at an angle relative to a posterior wall of the coronary vessel.

49. The method of claim 45, wherein the guide device is a guidewire.

50. The method of claim 45, wherein the dilator includes a bleed hole.

51. The method of claim 45, wherein the dilator includes a depth indication mechanism.

52. The method of claim 45, wherein the conduit is threaded.

53. The method of claim 45, wherein the conduit is nonthreaded.

54. The method of claim 45, wherein the conduit is in position over the dilator during the inserting of the dilator.

* * * * *

UNITED STATES PATENT AND TRADEMARK OFFICE
CERTIFICATE OF CORRECTION

PATENT NO. : 6,638,237 B1
DATED : October 28, 2003
INVENTOR(S) : Marvin Guiles et al.

It is certified that error appears in the above-identified patent and that said Letters Patent is hereby corrected as shown below:

Title page,
Item [57], ABSTRACT,
Line 19, replace "blood flow" with -- blood flows --;

Column 7,
Line 56, after "heart wall" delete ";".

Signed and Sealed this

Sixth Day of January, 2004

JAMES E. ROGAN
*Director of the United States Patent and Trademark Office*